(12) United States Patent
Yokozawa et al.

(10) Patent No.: US 6,472,539 B1
(45) Date of Patent: Oct. 29, 2002

(54) PRODUCTION PROCESS OF DIPHOSPHINE OXIDE AND DIPHOSPHONATE

(75) Inventors: Tohru Yokozawa, Kanagawa (JP); Takao Saito, Kanagawa (JP); Noboru Sayo, Kanagawa (JP); Takero Ishizaki, Shizuoka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/899,207

(22) Filed: Jul. 6, 2001

(51) Int. Cl.⁷ .............................. C07F 9/40; C07F 9/655
(52) U.S. Cl. ....................................... 549/220
(58) Field of Search ......................... 549/220

(56) References Cited

U.S. PATENT DOCUMENTS 5,872,273 A    2/1999   Saito et al. .................. 556/21
6,162,929 A   12/2000   Foricher et al. ............... 546/6

FOREIGN PATENT DOCUMENTS

| JP | 2000016997 | * | 1/2000 |
| JP | 2000016998 | * | 1/2000 |

\* cited by examiner

*Primary Examiner*—Bernard Dentz
(74) *Attorney, Agent, or Firm*—Sughrue Mion, PLLC

(57) ABSTRACT

A process for producing a diphosphine oxide or diphosphonate represented by formula (1) as defined, which comprises treating, with a base, a phosphine compound represented by formula (2) as defined and adding the thus-treated phosphine compound to a nonpolar solvent having an oxidative metal compound suspended therein so as to effect dimerization. The present invention makes it possible to produce, conveniently, in a high yield and safely, a diphosphine oxide or diphosphonate which is an intermediate for producing a diphosphine compound useful as a ligand of a metal complex serving as a catalyst for asymmetric synthesis reaction.

13 Claims, No Drawings

PRODUCTION PROCESS OF DIPHOSPHINE OXIDE AND DIPHOSPHONATE

FIELD OF THE INVENTION

The present invention relates to a novel process for practically and conveniently producing a diphosphine oxide or diphosphonate. More specifically, the invention pertains to a novel process for practically and conveniently producing a diphosphine oxide or diphosphonate which is an intermediate for the synthesis of an optically active phosphine compound serving as an important component of an excellent catalyst for asymmetric synthesis reaction.

BACKGROUND ART

A number of reports have hitherto been made on transition metal complexes usable for asymmetric synthesis such as asymmetric hydrogenation reaction, asymmetric isomerization reaction or asymmetric hydrosilylation reaction. Among them, complexes of a transition metal such as ruthenium, rhodium, iridium or palladium each having an optically active tertiary phosphine compound as a ligand are known to have an excellent performance as a catalyst for asymmetric synthesis reaction.

In order to heighten the performance of these complexes as a catalyst for asymmetric synthesis reaction, phosphine compounds of various structures have so far been developed and reported (for example, The Chemical Society of Japan, ed., "Kagakusousetsu 32: Yuukikinzokusakutai no Kagaku", 232–237 (1982); Ryoji Noyori, "Asymmetric Catalysis In Organic Synthesis", A Wiley-Interscience Publications). Among these various optically active phosphine compounds so far reported, 2,2'-bis(diphenylphosphino)-1,1'-binaphthyl (which will hereinafter be abbreviated to "BINAP") is one of excellent ligands of metallic complexes. A rhodium complex (JP-B-55-61973) and a ruthenium complex (JP-B-61-6390) containing this BINAP as a ligand have already been reported.

A process for synthesizing the above-described BINAP by brominating a racemic binaphthol by using a triphenylphosphine-dibromide at a high temperature (240 to 320° C.), introducing it to the corresponding digrignard reagent, condensing the reagent with a diarylphosphinyl chloride compound to form the corresponding diphosphine oxide compound and, after optical resolution, reducing it into the corresponding tertiary diphosphine compound (a BINAP) by using a trichlorosilane as a reducing agent is known as an industrial process (H. Takaya, K. Mashima, K. Koyano, M. Yagi, H. Kumobayashi, T. Taketomi, S. Akutagawa, R. Noyori, "J. Org. Chem., 51, 629 (1986)).

As another known process for synthesizing a diphosphine compound is a process of reducing a substituted (2-nitrophenyl)diphenylphosphine oxide compound into the corresponding (2-aminophenyl)diphenylphosphine oxide compound, diazotizing and iodinating the resulting compound into the corresponding substituted (2-iodophenyl) diphenylphosphine oxide compound, dimerizing the resulting compound in the presence of copper into the corresponding diphosphine oxide compound, and after optical resolution, reducing it into the corresponding tertiary diphosphine compound by using trichlorosilane as a reducing agent (Japanese Language Laid-Open Publication (PCT) No. Hei 5-507503).

A process for obtaining a diphosphine oxide compound by reacting a phosphine oxide compound with a lithium or magnesium amide compound, and adding an oxidative metal salt to the resulting suspension is also known as a process for synthesizing a diphosphine oxide compound (JP-B-11-246576).

The conventionally known processes for producing a diphosphine compound are however accompanied with the drawbacks that a long production step is sometimes required depending on an intermediate used for its synthesis; this process includes a severe exothermic reaction; a yield of a desired optically active diphosphine compound is low; or this process is not utterly safe upon industrialization.

Synthesis of a diphosphine oxide or diphosphonate which is an intermediate for the production of a diphosphine compound also involves various problems upon industrialization such as long production step, low yield, and inclusion of a dangerous step generating severe heat.

For example, a process described in the above-described JP-B-11-246576 is dangerous because marked heat generation is recognized when an oxidative metal compound is added to a base-treated phosphine oxide. Addition of an oxidative metal compound, particularly, anhydrous ferrous chloride which is presumed to be particularly important, in portions for suppressing this heat generation is disadvantageous as an industrial operation, because this metal compound itself has high hygroscopicity.

There is accordingly a demand for the development of a practical and industrially-suited process for conveniently producing a diphosphine oxide or diphosphonate in a high yield, which process does not need a long preparation step, and is free of severe heat generation.

SUMMARY OF THE INVENTION

An object of the present invention is to provide a novel, safe and practical process for producing, easily in a high yield without generating severe heat, a diphosphine oxide or diphosphonate compound which is useful as an intermediate for the synthesis of a diphosphine compound useful as a ligand constituting a metallic complex catalyst having excellent performances such as chemical selectivity, enantioselectivity and catalytic activity in asymmetric synthesis reaction, particularly asymmetric hydrogenation reaction.

In order to achieve the above objects, the present inventors made extensive studies. As a result, it has been found that a diphosphine oxide or diphosphonate such as ((5,6), (5',6')-bis(methylenedioxy)biphenyl-2,2'-diyl)bis (diphenylphosphine oxide) (which will hereinafter be abbreviated as "SEGPHOSO") or ((5,6),(5',6')-bis (methylenedioxy)biphenyl-2,2'-diyl)bis (diphenylphosphonate) can be synthesized in a short step, safely and in a high yield while suppressing a marked heat generation reaction, for example, by suspending an oxidative metal compound such as ferric chloride in a nonpolar solvent such as toluene, adding thereto a reaction mixture obtained by treating a phosphine or phosphonate such as diphenyl(3,4-methylenedioxyphenyl)phosphine oxide or diphenyl(3,4-methylenedioxyphenyl)phosphonate with a base such as lithium diisopropylamide and reacting them, leading to the completion of the invention.

In a first aspect of the present invention, there is thus provided a process for producing a diphosphine oxide or diphosphonate represented by the following formula (1):

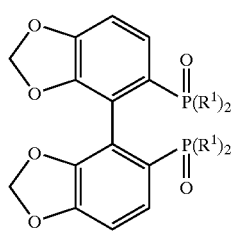

(1)

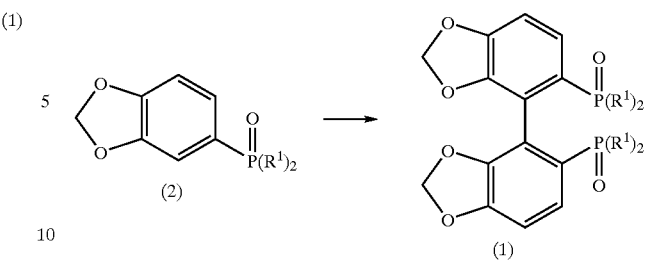

wherein, $R^1$ represents a $C_{1-4}$ alkyl group, a $C_{5-8}$ cycloalkyl group, a phenyl group, a substituted phenyl group substituted with 1 to 5 substituents which may be the same or different and each selected arbitrarily from the group consisting of $C_{1-4}$ alkyl groups, $C_{1-4}$ alkoxy groups and a phenyl group, a naphthyl group which may be substituted with a $C_{1-4}$ alkyl group or a $C_{1-4}$ alkoxy group, a $C_{1-4}$ alkoxy group, a phenoxy group, or a substituted phenoxy group substituted with 1 to 5 substituents which may be the same or different and each selected arbitrarily from the group consisting of $C_{1-4}$ alkyl groups, $C_{1-4}$ alkoxy groups and a phenyl group, which comprises treating, with a base, a phosphine oxide or phosphonate compound represented by the following formula (2):

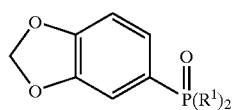

(2)

wherein, $R^1$ has the same meaning as described above, and adding the thus-treated compound to a nonpolar solvent having an oxidative metal compound suspended therein so as to effect dimerization.

In a second aspect of the invention, there is also provided a process for producing a diphosphine oxide or diphosphonate represented by the formula (1), wherein in the above-described first invention, the base is selected from the group consisting of organolithium reagents, organomagnesium reagents such as Grignard reagents and magnesiumamides.

In a third aspect of the invention, there is also provided a process for producing a diphosphine oxide or diphosphonate represented by the formula (1), wherein in the above-described first invention, the oxidative metal compound is at least one selected from the group consisting of metal salts and metallic complex compounds each made of iron, copper, ruthenium, cobalt, nickel, vanadium, molybdenum, manganese or titanium.

In a fourth aspect of the invention, there is also provided a process for producing a diphosphine oxide or diphosphonate represented by the formula (1), wherein in the above-described first invention, the nonpolar solvent to have an oxidative metal compound suspended therein is at least one selected from the group consisting of aliphatic hydrocarbons and aromatic hydrocarbons.

The production process of the above-described inventions can be indicated by the following reaction scheme:

The diphosphine oxide or diphosphonate represented by the above-described formula (1) will next be described more specifically. With regards to $R^1$ in the formula, examples of the $C_{1-4}$ alkyl group include methyl, ethyl, propyl, isopropyl, n-butyl, isobutyl, sec-butyl and t-butyl; those of the $C_{5-8}$ cycloalkyl group include cyclopenthyl, 2,5-dimethylcyclopenthyl, 3,4-dimethylcyclopenthyl, cyclohexyl, 4-methylcyclohexyl, 2,6-dimethylcyclohexyl, 3,5-dimethylcyclohexyl, 4,4-dimethylcyclohexyl and cycloheptyl; those of the phenyl or substituted phenyl include phenyl, p-tolyl, p-methoxyphenyl, p-trifluoromethylphenyl, p-fluorophenyl, p-dimethylaminophenyl, p-t-butylphenyl, 3,5-dimethylphenyl, 3,5-di-t-butylphenyl, 3,4,5-trimethoxyphenyl, 3,5-dimethyl-4-methoxyphenyl, 3,5-di-t-butyl-4-methoxyphenyl, 3,5-ditrifluoromethylphenyl, 3,5-dichlorophenyl, 3,5-difluorophenyl, pentafluorophenyl and biphenyl; those of the naphthyl or substituted naphthyl include α-naphthyl, β-naphthyl, 6-methoxy-α-naphthyl and 6-methoxy-β-naphthyl; those of the $C_{1-4}$ alkoxy group include methoxy, ethoxy, propoxy, isopropoxy, n-butoxy, isobutoxy, sec-butoxy and t-butoxy; and those of the phenyloxy or substituted phenyloxy group include phenyloxy, p-tolyloxy and p-methoxyphenyloxy.

The diphosphine oxide or diphosphonate represented by the formula (1) is preferred as an intermediate for producing a diphosphine compound useful as a catalyst for asymmetric synthesis reaction. Specific examples of such a compound include:

(a) (±)-((5,6),(5',6')-bis(methylenedioxy)biphenyl-2,2'-diyl) bis(diphenylphosphine oxide) (SEGPHOSO), (b) (±)-((5,6),(5',6')-bis(methylenedioxy)biphenyl-2,2'-diyl) bis(bis(3,5-dimethylphenyl)phosphine oxide), (c) (±)-((5,6),(5',6')-bis(methylenedioxy)biphenyl-2,2'-diyl) bis(bis(3,5-di-t-butyl-4-methoxyphenyl)phosphine oxide), (d) (±)-((5,6),(5',6')-bis(methylenedioxy)biphenyl-2,2'-diyl) bis(bis(4-methoxyphenyl)phosphine oxide), (e) (±)-((5,6),(5',6')-bis(methylenedioxy)biphenyl-2,2'-diyl) bis(dicyclohexylphopshine oxide), (f) (±)-((5,6),(5',6')-bis(methylenedioxy)biphenyl-2,2'-diyl) bis(bis(3,5-di-t-butylphenyl)phosphine oxide), and (g) (±)-((5,6),(5',6')-bis(methylenedioxy)biphenyl-2,2'-diyl) bis(diphenyl phosphonate).

Production processes of the invention including that of a phosphine oxide or phosphonate represented by the above-described formula (2) will next be described more specifically.

In the first place, a phosphine oxide represented by the formula (2) can be synthesized by a process analogous to a known process, for example, that described in J. J. Monagle, et al., "Journal of Organic Chemistry, 32, 2477 (1967)".

A phosphonate compound represented by the formula (2) can be synthesized easily by a process known per se in the art or an analogous process thereto. One of the examples of the production process is to add dropwise a chlorophosphate compound represented by the formula (3):

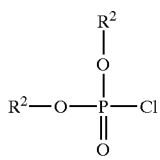

(3)

wherein, R² represents a $C_{1-4}$ alkyl group, a phenyl group or a substituted phenyl group substituted with 1 to 5 substituents which may be the same or different and are selected arbitrarily from the group consisting of $C_{1-4}$ alkyl groups, $C_{1-4}$ alkoxy groups and a phenyl group to a solution of a Grignard reagent or lithium reagent represented by the following formula (4):

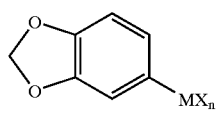

(4)

wherein, M represents magnesium or lithium, X represents a halogen atom and n stands for 0 or 1, in tetrahydrofuran, dioxane, ether, toluene or hexane at 30 to 40° C. and reacting them at room temperature for 12 to 18 hours. Compounds employed for the above-described synthesis are easily available by the ordinary preparation process.

In the present invention, prior to dimerization of a phosphine oxide or phosphonate represented by the formula (2), it is anionized. This anion formation can be conducted in a manner known per se in the art. One of the examples is to react a phosphine oxide compound or phosphonate compound with at least 1 equivalent, preferably 1.2 to 2.0 equivalents of a base selected from organolithium reagents, organomagnesium reagents such as Grignard reagents and magnesiumamides in a solvent such as ether, aliphatic hydrocarbon or aromatic hydrocarbon, or mixture thereof at −5° C., preferably −78 to −15° C.

Examples of the organolithium reagent include lithium alkyl amides, alkyl lithiums and allyl lithiums; those of the organomagnesium reagent include magnesium alkyl amides. Preferred examples of the base selected from these organolithium reagents, Grignard reagents and organomagnesium reagents include lithium diethyl amide, lithium diisopropyl amide (which will hereinafter be abbreviated as "LDA"), methyl lithium, butyl lithium, phenyl lithium, $C_{1-5}$ alkyl magnesium halides, substituted or unsubstituted phenyl magnesium halides, magnesium diethyl amide and magnesium diisopropyl amide. Among them, LDA is more preferred.

Preferred examples of the ether, aliphatic hydrocarbon or aromatic hydrocarbon solvent include tetrahydrofuran (which will hereinafter be abbreviated as "THF"), dioxane, diethyl ether, toluene, hexane and heptane, of which THF is more preferred.

The target product, that is, diphosphine oxide or diphosphonate represented by the formula (1) can be prepared in the following manner. Described specifically, the anion solution prepared in the above-described manner is reacted at 50° C. or less, preferably −5 to 15° C. with a mixture obtained by suspending at least 1 equivalent, more preferably 1.2 to 2.0 equivalents (the number of the equivalent may be the same or different from the equivalent of the base) of an oxidative metal compound in an aliphatic or aromatic hydrocarbon.

The above-described oxidative metal compound is selected from oxidative salts or complex compounds of a metal selected from iron, copper, ruthenium, cobalt, nickel, vanadium, molybdenum, manganese or titanium, that is, oxidizing agents. Preferred examples of such an oxidative compound include salts and complex compounds of a metal selected from trivalent iron, divalent copper, trivalent ruthenium, trivalent cobalt, divalent nickel, trivalent, tetravalent, pentavalent vanadium, trivalent, tetravalent, pentavalent or hexavalent molybdenum, trivalent, tetravalent, pentavalent or hexavalent manganese and trivalent or tetravalent titanium. More preferred are chlorides, bromides, iodides, nitrates, sulfates, perchlorates, acetates, oxalates or acetylacetone complexes of such a metal, bipyridyl or phenanthrene complex of such a metal salt, with iron trichloride, iron tribromide, iron triiodide, copper dichloride, copper dibromide and copper diiodide being further more preferred.

Examples of the aliphatic or aromatic hydrocarbon which is a nonpolar solvent for suspending therein an oxidative metal compound include pentane, hexane, heptane, octane, cyclohexane, methylcyclohexane, benzene, toluene and xylene, of which toluene is particularly preferred.

A description will next be made of a novel production process of a diphosphine oxide compound according to the invention by using, as a typical example, the production process of, among the compounds embraced by the invention, SEGPHOSO represented by the below-described formula (5) (wherein, Ph represents a phenyl group) which is an intermediate useful for the preparation of (−) or (+)-((5,6),(5',6')-bis(methylenedioxy)biphenyl-2,2'-diyl)bis (diphenylphosphine) (which will hereinafter be abbreviated to "SEGPHOS") in order to simplify this description. It should however be borne in mind that this example is merely a typical example of the invention and the invention is not limited to it.

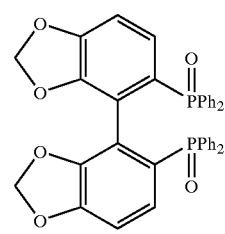

(5)

Diphenyl(3,4-methylenedioxyphenyl)phosphine oxide represented by the following formula (7) is prepared by adding dropwise a tetrahydrofuran solution of one equivalent of 3,4-methylenedioxybromobenzene represented by the following formula (6) to a magnesium piece at 40° C. or less, reacting them at room temperature for at least 3 hours to form a Grignard reagent, adding one equivalent of diphenylphosphinyl chloride to the resulting Grignard reagent at 40° C. or less, and reacting them at room temperature for 12 to 18 hours.

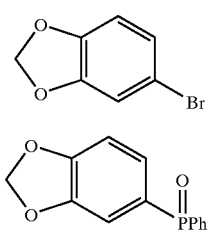

(6)

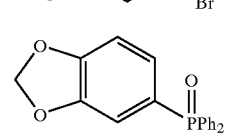

(7)

Alternatively, the diphenyl(3,4-methylenedioxyphenyl) phosphine oxide represented by the formula (7) can be prepared by the following process.

That is, diphenyl(3,4-methylenedioxyphenyl) phosphonate represented by the following formula (8) is prepared by adding dropwise a tetrahydrofuran solution of one equivalent of 3,4-methylenedioxybromobenzene (6) to a magnesium piece at 40° C. or less, reacting them at room temperature for at least 3 hours to form a Grignard reagent, adding the resulting reagent to a THF solution of one equivalent of diphenylphosphoryl chloride, and reacting them at room temperature for 12 to 18 hours. Then, to this compound, a THF solution of 2.5 equivalents of phenylmagnesium bromide is added dropwise at 5° C. or less and they are reacted at room temperature for at least 12 to 18 hours, whereby the diphenyl(3,4-methylenedioxyphenyl) phosphine oxide (7) is prepared.

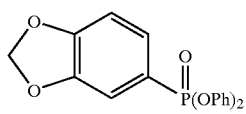

(8)

The resulting phosphine oxide (7) is then dissolved in THF and a THF solution of 1.2 equivalents of lithium diisopropyl amide is allowed to act on the resulting solution at −15° C. The reaction mixture is added dropwise to a toluene suspension of 1.2 equivalents of iron trichloride (anhydride) at a rate maintaining the temperature at 5° C. of less and they are reacted, whereby the target SEGPHOSO can be produced in a high yield.

The production process of the invention makes it possible to conveniently prepare, in a high yield, a diphosphine oxide or diphosphonate represented by the formula (1) by a short step without generating severe heat. The process of the invention is therefore industrially useful for the production of an intermediate for the synthesis of an optically active phosphine compound, particularly SEGPHOS, which serves as an important component of a catalyst for asymmetric synthesis reaction.

The present invention will hereinafter be described in further detail by Examples. It should however be borne in mind that the invention is not limited by them.

Following are apparatuses used for the measurement of physical properties in the following Examples and Comparative Examples.

Nuclear magnetic resonance $^1$H NMR

Bruker AM400 (400 MHz)

$^{31}$P NMR

Bruker AM400 (160 MHz)

Yanaco MP-500D

Melting point

High-performance liquid chromatography HPLC

Apparatus: LC10AT&SPD10A (Shimadzu Corporation)

Column: Inertsil 100-5 (4.6×230 mm) (GL Science)

Eluate: hexane:2-propanol=95:5

Flow rate: 0.5 ml/min

Detection wavelength: 254 nm

EXAMPLE 1

Synthesis of (5,6),(5',6')-bis(methylenedioxy) biphenyl-2,2'-diyl)bis(diphenylphosphine oxide)

After purging the inside of a 1-L four-necked flask with nitrogen, 40 ml (0.28 mol) of diisopropylamine and 200 ml of THF were added. Under cooling with ice-salt (the internal temperature became −5° C.), 175 ml (0.279 mol) of a 1.7M n-butyl lithium solution was added dropwise over 30 minutes (heat generation to 0 to 5° C. occurred). The mixture was then stirred for about 2 hours at −5° C. The reaction mixture was cooled to −15° C. by acetone-dry ice (the internal temperature became −12 to −10° C.), followed by the dropwise addition of 300 ml of a THF solution of 75.22 g (0.233 mol) of diphenyl(3,4-methylenedioxyphenyl) phosphine oxide over 15 minutes. The internal temperature at this time was maintained at −10 to −5° C. Stirring was conducted at −12° C. for 15 minutes to prepare a lithium reagent.

On the other hand, after purging the inside of a 3-L four-necked flask with nitrogen, 45.79 g (0.282 mol) of ferric chloride (anhydride) was weighed. Then, 300 ml of toluene was added. The mixture was stirred for approximately 30 minutes under cooling with ice-water (the internal temperature became 5° C.). The lithium reagent prepared above was added over 30 minutes through a cannula (the internal temperature increased even to 12° C.). The mixture was stirred overnight at room temperature. After completion of the reaction was confirmed by HPLC, THF was distilled off under reduced pressure. To the residue were added 500 ml of a 10% aqueous hydrochloric acid solution and 500 ml of methylene chloride to terminate the reaction. After stirring for about 1 hour, the organic layer was separated from the water layer. The water layer was re-extracted with 300 ml of methylene chloride. Both the organic layers were mixed. The mixture was washed three times each with 1 liter of a 10% aqueous hydrochloric acid solution, and twice each with 500 ml of water, dried over magnesium sulfate and distilled under reduced pressure to remove the solvent, whereby 101.10 g of a crude product was obtained. To the resulting crude product was added 200 ml of ethyl acetate. After dissolving the former in the latter by heating, the solution was cooled to room temperature. Crystal seeds were added to the solution and the mixture was allowed to stand overnight at 5° C. The crystals thus precipitated were collected by filtration and dried under reduced pressure, whereby 66.50 of the title compound was obtained.

Yield: 88.6% m.p.: 230 to 232° C.

$^1$H-NMR (CDCl$_3$): δ5.26 (2H, d, J=1.5 Hz), 5.72 (2H, d, J=1.6 Hz), 6.65 (2H, dd, J=8.1, 2.1 Hz), 6.77 (2H, dd, J=14.1, 8.1 Hz), 7.28–7.72 (20H, m)

$^{31}$P-NMR (CDCl$_3$): δ29.6

EXAMPLE 2

Synthesis of (±)-(5,6),(5',6')-bis(methylenedioxy) biphenyl-2,2'-diyl)bis(diphenyl phosphonate)

Under a nitrogen gas stream, 500 ml (0.80 mol) of a 1.6N normal-butyl lithium solution was added dropwise to 600 ml of a THF solution of 115 ml (0.88 mol) of diisopropylamine cooled over an ice bath. After completion of the dropwise addition, stirring was continued for 2 hours to prepare LDA. The LDA thus prepared was then added to a 1.5 liter THF solution of 234 g (0.66 mol) of diphenyl(3,4-methylenedioxyphenyl)phosphonate at −60° C. The mixture was stirred for 45 minutes to prepare a lithium reagent.

On the side, after purging the inside of a 3-L four-necked flask with nitrogen, 128.0 g (0.80 mol) of ferric chloride (anhydride) was weighed. Then, 300 ml of toluene was added. The mixture was stirred for approximately 30 minutes under cooling with ice-water (the internal temperature became 5° C.). The lithium reagent prepared above was added over 30 minutes through a cannula (the internal temperature increased even to 12° C.). The mixture was stirred overnight at room temperature. After completion of the reaction was confirmed by HPLC, THF was distilled off under reduced pressure. To the residue were added 500 ml of a 10% aqueous hydrochloric acid solution and 500 ml of methylene chloride to terminate the reaction. After stirring for about 1 hour, the organic layer was separated from the water layer. The water layer was re-extracted with 300 ml of methylene chloride. Both the organic layers were mixed. The mixture was washed three times each with 1 liter of a 10% aqueous hydrochloric acid solution, and twice each with 500 ml of water, dried over magnesium sulfate and distilled under reduced pressure to remove the solvent, whereby 250.70 g of a crude product was obtained. The resulting crude product was recrystallized from acetonitrile, whereby 172.0 g of the title compound was obtained.

Yield: 77.10% m.p.: 119 to 123° C.

$^1$H-NMR (CDCl$_3$): δ5.54 (2H,d,J=1.4 Hz), 5.90(2H,d,J= 1.4 Hz), 6.77–6.94(8H,m), 6.97(2H,dd,J=8.1,3.5 Hz), 7.01–7.08(4H,m), 7.08–7.20(8H,m), 7.82(2H,dd,J=15.7,8.1 Hz)

$^{31}$P-NMR (CDCl$_3$): δ10.5

Reference Example 1

Synthesis of (±)-(5,6),(5',6')-bis(methylenedioxy) biphenyl-2,2'-diyl)bis(diphenyl phosphine oxide)

Under a nitrogen gas stream, 28 ml of a THF solution of 0.5N phenylmagnesium bromide (14 mmol) was added dropwise at room temperature to 10 ml of a THF solution of 1.0 g (1.42 mmol) of the (5,6), (5',6')-bis(methylenedioxy) biphenyl-2,2'-diyl)bis(diphenyl phosphonate) obtained in Example 2. The mixture was then reacted by stirring it overnight at room temperature. Water was added to quench an excess amount of the Grignard reagent. The solvent was distilled off under reduced pressure. Ethyl acetate (100 ml) and 1N hydrochloric acid (100 ml) were added to the residue, followed by stirring. The organic layer obtained by separation was washed with saturated saline, dried over magnesium sulfate and distilled under reduced pressure to remove the solvent, whereby a crude product was obtained. The crude product was purified by a silica gel column to yield the title compound (0.73 g).

Yield: 81% m.p.: 230 to 232° C.

$^1$H-NMR (CDCl$_3$): δ5.26 (2H,d,J=1.5 Hz), 5.72 (2H,d,J= 1.6 Hz), 6.65(2H,dd,J=8.1,2.1 Hz), 6.77(2H,dd,J=14.1,8.1 Hz), 7.28–7.72(20H,m)

$^{31}$P-NMR (CDCl$_3$): δ29.6

In Comparative Examples, reaction was conducted under similar conditions to Example 1 or Example 2 except a process of Comparative Examples is contrary to that of Examples wherein reaction is conducted by adding an anionic solution to an oxidative metal oxidizing agent suspended in a nonpolar solvent, in other words, in Comparative Examples, reaction is conducted by adding an oxidative metal compound to an anionic solution.

Comparative Example 1

Synthesis of ((5,6),(5',6')-bis(methylenedioxy)biphenyl-2,2'-diyl)bis(diphenylphosphine oxide)

After purging the inside of a 200-ml four-necked flask with nitrogen, 4.0 ml (28 mol) of diisopropylamine and 20 ml of THF were added. Under cooling with ice-salt (the internal temperature became −5° C.), 17.5 ml (28 mol) of a 1.7M n-butyl lithium solution was added dropwise over 30 minutes (heat generation to 0 to 5° C. occurred). The reaction mixture was then stirred for about 2 hours at −5° C. The reaction mixture was cooled to −15° C. by acetone-dry ice (the internal temperature became −12 to −10° C.), followed by the dropwise addition of 30 ml THF solution of 7.5 g (23 mmol) of diphenyl(3,4-methylenedioxyphenyl) phosphine oxide over 15 minutes. The internal temperature at this time was maintained at −10 to −5° C. Stirring was conducted at −12° C. for 15 minutes to prepare a lithium reagent.

The resulting lithium reagent was cooled to −15° C., to which 4.6 g (28 mmol) of ferric chloride (anhydride) was added in portions (severe heat generation was recognized at this time and the reaction temperature increased even to 30° C.). The reaction mixture was then stirred overnight at room temperature. After disappearance of the raw material phosphine oxide was confirmed by HPLC, THF was distilled off under reduced pressure. To the residue were added 50 ml of a 10% aqueous hydrochloric acid solution and 50 ml of methylene chloride to terminate the reaction. After stirring for about 1 hour, the reaction mixture was separated into the organic layer and the water layer. The water layer thus obtained was re-extracted with 30 ml of methylene chloride. Both the organic layers were mixed. The mixture was washed three times each with 100 ml of a 10% aqueous hydrochloric acid solution, and twice each with 50 ml of water, dried over magnesium sulfate and distilled under reduced pressure to remove the solvent, whereby 7.7 g of a crude product was obtained. The resulting crude product was purified by a silica gel column, whereby 4.3 g of the title compound was obtained in a yield of 57%.

Comparative Example 2

Synthesis of (5,6),(5',6')-bis(methylenedioxy) biphenyl-2,2'-diyl)bis(diphenyl phosphonate)

After purging the inside of a 300-ml four-necked flask with nitrogen, 11.5 ml (88 mmol) of diisopropylamine and 60 ml of THF were added. Under cooling with ice-salt (the internal temperature became −5° C.), 50.0 ml (80.0 mmol) of a 1.6M n-butyl lithium solution was added dropwise over 30 minutes (heat generation to 0 to 5° C. occurred). Stirring was conducted at −5° C. for approximately 2 hours. The reaction mixture was cooled to −60° C. by acetone-dry ice, followed by the dropwise addition of a 150 ml THF solution of 23.5 g (66 mmol) of diphenyl (3,4-methylenedioxyphenyl)phosphonate over 15 minutes. The reaction mixture was then stirred at −30° C. for 45 minutes, whereby a lithium reagent was prepared.

The lithium reagent thus obtained was cooled to −15° C. and 12.8 g (80 mmol) of ferric chloride (anhydride) was added in portions (a marked heat generation was recognized at this time and the reaction temperature increased even to 38° C.). Stirring was then conducted overnight at room temperature. After disappearance of the raw material phosphonate by HPLC, THF was distilled off under reduced pressure. The reaction was then terminated by the addition of 20 ml of a 10% aqueous hydrochloric acid solution and 200 ml of methylene chloride. After stirring for about 1 hour, the reaction mixture was separated into an organic layer and a water layer. The water layer thus obtained was re-extracted with 100 ml of methylene chloride. Both the organic layers were combined, washed three times each with 200 ml of a 10% aqueous hydrochloric acid solution and twice each with 100 ml of water, dried over magnesium sulfate and distilled under reduced pressure to remove the solvent to yield 17.8 g of the crude product. The crude product was purified by a silica gel column, whereby 7.5 g of the title compound was obtained in a yield of 32%.

As is apparent from Examples 1–2 and Comparative Examples 1–2, a target dimer was available in a high yield by adding an anionic solution to an oxidative metal oxidizing agent suspended in a nonpolar solvent, thereby effecting dimerization. When dimerization was conducted by adding an oxidative metal oxidizing agent to an anionic solution, on the other hand, a marked heat generation was recognized upon reaction and even though a target product was available by this process, the yield was as low as 57% or 32%.

Thus, dimerization reaction by adding an anionic solution to an oxidative metal oxidizing agent suspended in a non-polar solvent is very useful for completion of the present reaction.

While the invention has been described in detail and with reference to specific embodiments thereof, it will be apparent to one skilled in the art that various changes and modifications can be made therein without departing from the spirit and scope thereof.

This application is based on Japanese patent applications No. 2000-1870 filed on Jan. 7, 2000, the entire contents thereof being hereby incorporated by reference.

What is claimed is:

1. A process for producing a diphosphine oxide or diphosphonate represented by the following formula (1):

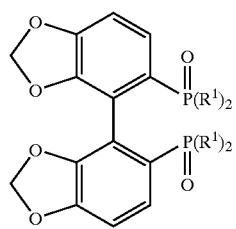

wherein, $R^1$ represents a $C_{1-4}$ alkyl group, a $C_{5-8}$ cycloalkyl group, a phenyl group, a substituted phenyl group substituted with 1 to 5 substituents which may be the same or different and each selected arbitrarily from the group consisting of $C_{1-4}$ alkyl groups, $C_{1-4}$ alkoxy groups and a phenyl group, a naphthyl group which may be substituted with a $C_{1-4}$ alkyl group or a $C_{1-4}$ alkoxy group, a $C_{1-4}$ alkoxy group, a phenyloxy group, or a substituted phenyloxy group substituted with 1 to 5 substituents which may be the same or different and each selected arbitrarily from the group consisting of $C_{1-4}$ alkyl groups, $C_{1-4}$ alkoxy groups and a phenyl group, which comprises treating, with a base, a phosphine oxide or a phosphonate compound represented by the following formula (2):

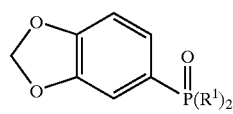

wherein, $R^1$ has the same meaning as defined above, and adding the thus-treated phosphine compound to a solvent which consists essentially of a non-polar solvent having an oxidative metal compound suspended therein so as to effect dimerization.

2. A process according to claim 1, wherein the base is selected from the group consisting of organolithium reagents and organomagnesium reagents.

3. A process according to claim 1, wherein the oxidative metal compound is at least one member selected from the group consisting of metal salts and metal complex compounds each made of iron, copper, ruthenium, cobalt, nickel, vanadium, molybdenum, manganese or titanium.

4. A process according to claim 1, wherein the nonpolar solvent is at least one member selected from the group consisting of aliphatic hydrocarbons and aromatic hydrocarbons.

5. A process according to claim 1, wherein the base is an organolithium reagent.

6. A process according to claim 1, wherein the oxidative metal compound is an iron salt.

7. A process according to claim 1, wherein the non-polar solvent is an aromatic compound.

8. A process according to claim 1, wherein the base is an organolithium reagent, the oxidative metal compound is an iron salt and the non-polar solvent is an aromatic compound.

9. A process according to claim 8, wherein the organolithium compound is a alkyl lithium, the oxidative metal compound is ferric chloride and the aromatic compound is toluene.

10. A process according to claim 1, wherein the treating with a base of the phosphine compound is conducted in a solvent.

11. A process according to claim 10, wherein in the solvent is tetrahydrofuran.

12. A process according to claim 9, wherein the treating with a base of the phosphine compound is conducted in a solvent.

13. A process according to claim 12, wherein in the solvent is tetrahydrofuran.

* * * * *